United States Patent [19]

Takatsuna et al.

[11] Patent Number: 4,927,953
[45] Date of Patent: May 22, 1990

[54] PROCESS FOR PREPARING AMINOPROPYL SILANES

[75] Inventors: Kazutoshi Takatsuna; Kouji Shiozawa; Yoshiharu Okumura, all of Iruma, Japan

[73] Assignee: Tonen Corporation, Tokyo, Japan

[21] Appl. No.: 404,964

[22] Filed: Sep. 11, 1989

[30] Foreign Application Priority Data

May 31, 1989 [JP] Japan .................................. 1-138181

[51] Int. Cl.$^5$ ................................................ C07F 7/10
[52] U.S. Cl. ........................................................ 556/413
[58] Field of Search ........................................... 556/413

[56] References Cited

U.S. PATENT DOCUMENTS

| 3,470,225 | 9/1969 | Kuorre et al. | 556/413 |
| 3,864,373 | 2/1975 | Seiler et al. | 556/413 |
| 4,481,364 | 11/1984 | Clue et al. | 556/413 |
| 4,556,222 | 12/1985 | Zuirk et al. | 556/413 |

FOREIGN PATENT DOCUMENTS 0284447  9/1988  European Pat. Off. ............ 556/413

Primary Examiner—Paul F. Shaver
Attorney, Agent, or Firm—Wenderoth, Lind & Ponack

[57] ABSTRACT

A process for preparing aminopropyl silanes comprises reacting an allylamine with a hydrosilane in the presence of a ruthenium compound having at least one tertiary phosphine ligand as a catalyst. By the proposed process the corresponding gamma-aminopropyl silane can be prepared in a high yield in a short period of reaction time.

4 Claims, No Drawings

PROCESS FOR PREPARING AMINOPROPYL SILANES

TECHNICAL FIELD OF THE INVENTION

The present invention relates to a process for preparing aminopropyl silanes such as aminopropyl alkoxy silanes. More particularly, it relates to a process for preparing aminopropyl silanes, in which a ruthenium compound having at least one tertiary phosphine ligand is used as a catalyst.

BACKGROUND OF THE INVENTION

Silane coupling agents are compounds having in their molecule an organic functional group and a hydrolizable group reactive with inorganic materials. Since the silane coupling agents are, due to their functional groups, capable of chemically bonding an organic polymer with an inorganic material, such as silica, thereby remarkably increasing the mechanical strength of the organic polymer, they are now indispensable in the development of ultrafashionable composite materials.

Aminopropyl silanes such as gamma-aminopropyl alkoxy silanes are used in the art as the silane coupling agent, and it is known that they can be prepared by hydrosilylation of an allylamine, which may be substituted on the nitrogen atom, with a hydrosilane.

For example, Japanese Patent Laid-open Publication No. 60-81189 discloses a process for the preparation of aminopropyl alkoxy silanes, which comprises reacting an allylamine with a hydrosilane using a platinum catalyst, such as chloroplatinic acid, in the presence of a promoter, such as anhydrous sodium carbonate. However, the reaction of an allylamine with a hydrosilane in the presence of a platinum catalyst, such as chloroplatinic acid, inevitably produces the corresponding beta-aminopropyl alkoxy silane, which may be referred to herein as the beta-isomer in addition to the desired gamma-aminopropyl alkoxy silane, which may be referred to herein as the gamma-isomer, normally with a ratio of the gamma-isomer to the beta-isomer of from 4 to 6, posing a problem in that the selectivity of the desired gamma-isomer is not satisfactorily high.

Japanese Patent Laid-open Publication No. 61-229885 discloses a process for the preparation of aminopropyl alkoxy silanes by reacting an allylamine with a hydrosilane in the presence of a catalyst comprising rhodium organic tertiary phosphine complex and optionally triphenylphosphine. By this process gamma-aminopropyl alkoxy silanes can be prepared in a high selectivity. The process is disadvantageous, however, in that a prolonged reaction time is required to achieve a high conversion. Further, an excessive amount of triphenylphosphine must be used to achieve a high selectivity of the gamma-isomer. Additionally, the rhodium compounds are so expensive that the aminopropyl alkoxy silanes cannot be produced on a industrial scale without reusing the rhodium compound recovered from the reaction mixture or decreasing an amount of the rhodium compound used. J. of Organomet. Chem., 149, 29–36 (1978) discloses the hydrosilylation of olefins in the presence of a metallic carbonyl catalyst, such as cobalt-, rhodium-, iridium- and iron-carbonyl compounds and teaches that N, N-dimethylaminopropyl triethoxy silane can be obtained in a high yield from N, N-dimethylallylamine and triethoxy silane. It is also stated in this article that when an olefinic amine, such as allylamine is hydrosilylated, the silylation proceeds preferentially on the amine nitrogen atom. This statement means that hydrosilylation of a N-unsubstituted allylamine with a hydrosilane would be unsuitable for the preparation of the corresponding aminopropyl alkoxy silane.

OBJECT OF THE INVENTION

The invention is intended to solve the problems involved in the prior art and an object of the invention is to provide a process for preparing aminopropyl silanes from a hydrosilane and an allylamine wherein gamma-aminopropyl silanes can be prepared in a high selectivity.

SUMMARY OF THE INVENTION

It has now been found that when an allylamine is reacted with a hydrosilane in the presence of a ruthenium compound having at least one tertiary phosphine ligand as a catalyst, the desired gamma-aminopropyl silanes can be prepared in a high yield and in a reasonable reaction time.

Thus, a process for preparing aminopropyl silanes according to the invention comprises reacting an allylamine of the formula [I]

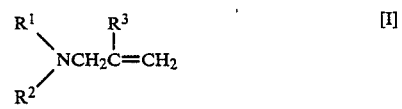

wherein $R^1$ and $R^2$, each represents hydrogen, alkyl having from 1 to 10 carbon atoms, alkenyl having from 2 to 10 carbon atoms, phenyl, substituted phenyl, $-CH_2CH_2NHCH_2CH_2NH_2$ or $-CH_2CH_2NH_2$, and $R^3$ is hydrogen or alkyl having from 1 to 6 carbon atoms with a hydrosilane in the presence of a ruthenium compound having at least one tertiary phosphine ligand as a catalyst.

DETAILED DESCRIPTION OF THE INVENTION

A process for preparing aminopropyl silanes according to the invention will be fully described hereinafter.

ALLYLAMINES

Allylamines represented by the formula [I] above as one of starting materials are used in the process according to the invention for preparing aminopropyl silanes. The substituents represented by $R^1$ and $R^2$ [I] are the same or different.

Examples of such allylamines include, for example, allylamine, N,N-dimethylallylamine, N,N-diethylallylamine, N-methylallylamine, N-ethylallylamine, 2-methylallylamine, diallylamine, allylethylenediamine, and N--allylaniline.

HYDROSILANES

In the process according to the invention the allylamine as described above is reacted with a hydrosilane. Hydrosilanes are compounds having at least one Si-H linkage in the molecule and may be represented by the following formulas [II], [III] or [IV]:

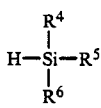

wherein $R^4$, $R^5$ and $R^6$ are the same or different and each represents alkyl or alkoxy;

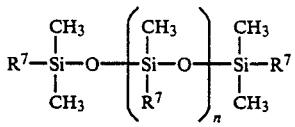

wherein each $R^7$ represents hydrogen or methyl with the proviso that at least one $R^7$ represents hydrogen, and n is an integer from 0 to 300; and

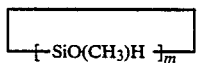

wherein m is an integer from 3 to 10.

Examples of hydrosilanes of the formulas [II], [III] and [IV] include, for example, triethoxy silane, trimethoxy silane, trimethylsilane, triethylsilane, tripropoxy silane, tributoxy silane, methyl dimethoxy silane, ethyl dimethoxy silane, methyl diethoxy silane, dimethyl methoxy silane, trioctyloxy silane, methyl dioctyloxy silane, dimethyl octyloxy silane, 1,1,3,3-tetramethyl-disiloxane, pentamethyldisiloxane, alpha, omega-dihydropolysiloxane, polysiloxanes having at least one Si - H linkage in the the polymer chain, 1,3,5,7-tetramethyl-cyclotetrasiloxane and 1,3,5,7,9-pentamethyl-cyclopentasiloxane.

CATALYST

When the allylamine as described above is reacted with the hydrosilane as described above according to the invention, a ruthenium compound having at least one tertiary phosphine ligand is used as a catalyst.

In the tertiary phosphine ligand, three substituents directly attached to the phosphorus atom are the same or different and may be alkyl groups, aryl groups or alkoxy groups. Furthermore, the ruthenium compounds having at least one tertiary phosphine ligand used herein may have organic or inorganic ligands such as carbonyl, halogen, hydrogen and olefin in addition to tertiary phosphine ligand.

Examples of the ruthenium compounds having at least one tertiary phosphine ligand include, for example, tricarbonyl-bis(triphenylphosphine) ruthenium
  $Ru(CO)_3(PPh_3)_2$,
dichloro-tris(triphenylphosphine) ruthenium
  $RuCl_2(PPh_3)_3$,
hydrido-chloro-tris(triphenylphosphine) ruthenium
  $RuHCl(PPh_3)_3$,
dihydrido-tetrakis(triphenylphosphine) ruthenium
  $RuH_2(PPh_3)_4$,
and ethylene-tris(triphenylphosphine) ruthenium
  $Ru(CH_2=CH_2)(PPh_3)_3$.

REACTION CONDITIONS

The allylamine and hydrosilane are preferably used in such amounts that a ratio of the allylamine to the hydrosilane by mole is within the range from about 1.3:1 to about 1:1.3.

The allylamine and hydrosilane are preferably used in the reaction after having impurities such as halogen and sulfur compounds removed as far as possible.

The reaction may be carried out under atmospheric or elevated pressure. The reaction is carried out at a temperature of not lower than 50° C., preferably from about 100° C. to about 200° C. If a reaction temperature is substantially below 50° C., a prolonged reaction time should be required, because the formation rate of the desired gamma-aminopropyl silanes decreased. Whereas, when the reaction temperature increases above 200° C., increasing amounts of the beta-isomer tend to be formed, undesirably lowering the selectivity of the gamma-isomer.

While the ruthenium compound as a catalyst may be used in an excess amount, it is sufficient to use the ruthenium compound in the reaction system in an amount of from $10^{-6}$ to $10^{-3}$ mole per mole of the allylamine, on a ruthenium basis.

In carrying out the reaction, solvents may or may not be used. When solvents are used, hydrocarbon solvents such as toluene, xylene, heptane and dodecane, or ethers such as tetrahydrofuran and 1,4-dioxane are preferred. The solvents may be used alone or in combination.

The reaction may be carried out in the presence of excess amounts of a neutral ligand which may be the same as or different from the neutral ligands coodinated to the ruthenium metal. For example, the gamma/beta ratio in the products tends to be improved if the reaction is carried out in the presence of excess amounts of triphenylphosphine.

While the reaction time greatly depends upon the reaction conditions, particularly reaction temperature, it may normally be from 3 to 5 hours.

When an allylamine is reacted with a hydrosilane in the presence of a ruthenium compound having at least one tertiary phosphine ligand as a catalyst, the corresponding gamma-aminopropyl silane can be produced in a high selectivity with little yield of the beta-isomer, leading to a high gamma/beta ratio. Further, the reaction rapidly proceeds, and thus, the gamma-isomer can be obtained in a yield as high as 60% or higher and in a gamma/beta ratio of more than 100 without the necessity of the presence of excess amount of the phosphine ligand.

In contrast, if an allylamine is reacted with a hydrosilane, using a chloroplatinic acid catalyst, the yield of the gamma-isomer is about 40–50%, and a gamma/beta ratio is about 4. Further, if an allylamine is reacted with a hydrosilane using a catalyst consisting solely of hydridocarbonyl tris(triphenylphosphine) rhodium complex as a catalyst, the gamma-isomer with a gamma/beta ratio of about 60 can only be obtained at the cost of a prolonged reaction time, e.g., 6 hours or more, owing to a slow reaction rate.

By a process for preparing aminopropyl silanes according to the invention, in which an allylamine is reacted with a hydrosilane in the presence of a ruthenium compound having at least one tertiary phosphine ligand as a catalyst, the corresponding gamma-aminopropyl silane can be prepared in a high selectivity and yield in a reasonable reaction time.

While the invention is illustrated by the following examples, the invention is not limited thereto.

EXAMPLE 1

A four-neck flask equipped with a reflux condenser, stirrer, dropping funnel and thermometer, was charged with 41 g of triethoxysilane (0.25 mole), 20 ml of p-xylene as a solvent and $2.5 \times 10^{-4}$ mole of tricarbonyl-bis(triphenylphosphine) ruthenium catalyst (0.1 mole % of Ru catalyst per mole of triethoxysilane). The resulting mixture was heated to a temperature under stirring by placing the flask on an oil bath maintained at a temperature of 110° C. To the heated mixture, 14 g of allylamine (0.25 mole) was dropwise added over a period of about one hour and the resulting mixture was maintained for further 3 hours under the same reaction conditions.

After completion of the reaction, the reaction mixture was subjected to gas chromatography analysis. It was revealed that gamma-aminopropyl triethoxy silane had been formed in a yield of 62%, while the yield of beta-aminopropyl triethoxy silane was 0.52% (each of the yield was determined on a basis of the triethoxysilane).

EXAMPLE 2

The reaction was carried out as in Example 1 except that 30.6 g of trimethoxysilane (0.25 mole) was used instead of the triethoxy silane and the toluene was replaced with xylene.

After completion of the reaction, the reaction mixture was subjected to gas chromatography analysis. It was revealed that the gamma-aminopropyl trimethoxy silane had been formed in a yield of 70%, while the yield of the beta-isomer was 0.7% (each of the yields was determined on a basis of the trimethoxy silane).

EXAMPLE 3

The reaction was carried out as in Example 1 except that 25.0 g of allylethylenediamine (0.25 mole) was used instead of the allylamine, the solvent was replaced with n-decane and an oil bath at a temperature of 150° C. was used.

After completion of the reaction, the reaction mixture was subjected to gas chromatography analysis. It was revealed that N-(2-aminoethyl)-3-aminopropyl triethoxy silane (gamma-isomer) had been formed in a yield of 60% on the allylethylenediamine basis.

EXAMPLE 4

The reaction was carried out as in Example 1 except that dichloro-tris(triphenylphosphine) ruthenium and N,N-dimethylallylamine were used instead of the tricarbonyl-bis(triphenylphosphine) ruthenium and the allylamine, respectively.

After completion of the reaction, the reaction mixture was subjected to gas chromatography analysis. It was revealed that N,N-dimethyl-gamma-aminopropyl triethoxy silane (gamma-isomer) had been formed in a yield of 81%, while the yield of N,N-dimethyl-1-methyl-beta-aminoethyl triethoxy silane (beta-isomer) was 0.7% (each of the yields was determined on a basis of the triethoxy silane).

EXAMPLE 5

Example 1 was repeated except that the triethoxysilane was replaced with 1,1,3,3-tetramethyldisiloxane, allylamine was used in a double amount, and the reaction was carried out for 1 hour.

After completion of the reaction, the reaction mixture was subjected to gas chromatography analysis. It was revealed that 1,3-bis(gamma-aminopropyl) tetramethyldisiloxane had been formed in a yield of 65% on a basis of the 1,1,3,3,-tetramethyldisiloxane.

CONPARATIVE EXAMPLE 1

Example 1 was repeated except that the catalyst was replaced with triruthenium dodecacarbonyl.

After completion of the reaction, the reaction mixture was subjected to gas chromatography analysis. It was revealed that gamma-aminopropyl triethoxy silane had been formed in a yield of 9% on a basis of the allylamine.

What is claimed is:

1. A process for preparing aminopropyl silanes which comprises reacting an allylamine of the formula [I]

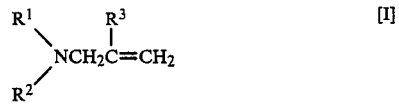

wherein $R^1$ and $R^2$, each represents hydrogen, alkyl having from 1 to 10 carbon atoms, alkenyl having from 2 to 10 carbon atoms, phenyl, substituted phenyl, $-CH_2CH_2NHCH_2CH_2NH_2$ or $-CH_2CH_2NH_2$, and $R^3$ is hydrogen or alkyl having from 1 to 6 carbon atoms with a hydrosilane in the presence of a ruthenium compound having at least one tertiary phosphine ligand as a catalyst.

2. The process as claimed in claim 1 wherein said ruthenium compound having at least one tertiary phosphine ligand is tricarbonyl-bis(triphenylphosphine) ruthenium, dichloro-tris(triphenylphosphine) ruthenium, hydridochloro-tris(triphenylphosphine) ruthenium, dihydrido-tetrakis(triphenylphosphine) ruthenium or ethylene-tris(triphenylphosphine) ruthenium.

3. The process as claimed in claim 1 wherein said ruthenium compound having at least one tertiary phosphine ligand is used in an amount of from $10^{-6}$ to $10^{-3}$ mole per mole of the allylamine.

4. The process as claimed in claim 1 wherein the reaction is carried out at a temperature of from about 100° C. to 200° C.

* * * * *